United States Patent [19]
Ruddy et al.

[11] Patent Number: 5,580,579
[45] Date of Patent: Dec. 3, 1996

[54] SITE-SPECIFIC ADHESION WITHIN THE GI TRACT USING NANOPARTICLES STABILIZED BY HIGH MOLECULAR WEIGHT, LINEAR POLY (ETHYLENE OXIDE) POLYMERS

[75] Inventors: Stephen B. Ruddy, Schwenksville; W. Mark Eickhoff, Downingtown; Gary Liversidge, West Chester, all of Pa.

[73] Assignee: Nano Systems L.L.C., Collegeville, Pa.

[21] Appl. No.: 388,878

[22] Filed: Feb. 15, 1995

[51] Int. Cl.⁶ .......................... A61K 9/107; A61K 123/00
[52] U.S. Cl. .......................... 424/489; 424/498; 514/937; 514/938; 514/939; 514/943
[58] Field of Search .................................. 424/4, 5, 489, 424/498; 514/937, 938, 939, 943

[56] References Cited

U.S. PATENT DOCUMENTS 5,145,684  9/1992  Liversidge et al. .................... 424/489

OTHER PUBLICATIONS

Kinam Park and Joseph R. Robinson, "Bioadhesive polymers as platforms for oral–controlled drug delivery: method to study bioadhesion", 1984, pp. 107–127.

Primary Examiner—Shep K. Rose
Attorney, Agent, or Firm—Rudman & Balogh

[57] ABSTRACT

Nanoparticulate crystalline therapeutic or diagnostic substances formulated with stabilizers and high molecular weight, linear poly(ethylene oxide) polymers, enhance contact between the crystalline therapeutic or diagnostic substances and the gastrointestinal tract providing site-specific and extended therapeutic or diagnostic effect.

15 Claims, No Drawings

SITE-SPECIFIC ADHESION WITHIN THE GI TRACT USING NANOPARTICLES STABILIZED BY HIGH MOLECULAR WEIGHT, LINEAR POLY (ETHYLENE OXIDE) POLYMERS

FIELD OF THE INVENTION

The present invention relates to therapeutic and diagnostic formulations for gastrointestinal agents in combination with high molecular weight, linear poly(ethylene oxide) polymers.

BACKGROUND OF THE INVENTION

In the delivery of certain slightly water-soluble drugs intended to act by contact with the mucosal surface of the gastrointestinal tract (hereinafter referred to as the GI tract) without substantial absorption therethrough into the blood stream, the problem of insufficient adherence and dwell time are often encountered. Drugs, such as antacids, antimicrobial and antifungal agents tend to pass through the GI tract without providing sufficient local preventive/active effects.

Accordingly, there is a need to provide oral GI formulations that are safe, efficacious and have sufficient dwell or contact time with the GI mucosa. Such formulations should have excellent mucosal coating properties for both the upper and lower GI tract, i.e., they should have mucoadhesive or bioadhesive properties that enable the entire GI tract to be coated. There also exists a need to provide formulations to specific regions within the GI tract. Since the slightly water-soluble drugs do not by themselves possess such bioadhesive or mucoadhesive properties, the formulations containing them must provide the same.

The identification of surface active stabilizers with bioadhesive or mucoadhesive properties that enable coating of the entire GI tract or specific regions within the GI tract with therapeutic agents has not been reported to date.

It is common medical practice to employ barium sulfate formulations to image the GI tract of patients. Barium sulfate can be given either orally or rectally to visualize the stomach and small intestine or rectally to visualize the large intestine. Barium sulfate is usually administered as a suspension that has limited stability even with the addition of stabilizers. As such, it often forms clumps that yield resultant radiopaque areas on X-ray films and provides for poor patient acceptability characteristics. Poor patient acceptability characteristics include palatability, patient discomfort during and after administration and prolonged constipation of the patient. Barium sulfate also shows poor affinity for coating the GI mucosa and consequently the patient is often manipulated or rotated to ensure the barium sulfate suspensions coat the gastric mucosa. Nevertheless, segments of the GI tract are often obscured or are not adequately coated, necessitating repeated examinations to achieve satisfactory imaging results.

Bioadhesion is usually achieved by interaction of either a synthetic or natural polymeric substance with the mucosal membranes of the GI tract. Such technology has been employed to enhance drug delivery by increasing the transit time of a drug substance in the GI tract and hence promoting an opportunity for enhanced absorption. With regard to the development of water insoluble of poorly water-soluble drug formulations intended to coat the GI tract, it is important to identify mucosal adhesives that coat the GI surfaces and affect diseased or abnormal tissues. Highly charged carboxylated polyanions are good candidates for use as bioadhesives in the GI tract. See, for example: Park, K. and Robinson, J. R., Bioadhesion: Polymers for Orally Controlled Drug Delivery; Method to Study Bioadhesion. Int. J. Pharm., 19, 107 (1984). The formation of a bioadhesive bond between a polymeric substance and the mucosal lining of the GI tract can be visualized as a two step process, i.e., initial contact between the two surfaces and the formation of secondary bonds due to non-covalent interactions. Bioadhesives specific for the GI tract must interact with the mucus layer during attachment. Mucus, a general term for the heterogeneous secretion found on epithelial surfaces of the GI tract, is made of the following components: glycoprotein macromolecules, inorganic salts, proteins, lipids, and mucopolysaccharides. These glycoproteins typically consist of a protein core with carbohydrate side chains. This forms a network of mucus that is a continuous layer covering the GI tract. From a bioadhesive perspective, mucus consists of highly hydrated, cross linked linear, flexible yet random coiled glycoprotein molecules with a net negative charge. Understanding the principals of bioadhesion is the basis for formulating oral or rectal compositions for coating portions of the GI tract. Bioadhesion accounts for the interaction between a biological surface and a biological substance. As noted previously, bioadhesive agents are usually polymeric substances that adhere to tissues by ionic or covalent bonds of by physical attachment. Several theories of bioadhesion have been published including electronic, adsorption, wetting, diffusion, and fracture theories. Bioadhesives bind to membrane surfaces and are retained for various periods of time.

We have discovered a certain class of polymers for promoting site specific bioadhesion or mucoadhesion within the GI tract. The polymers provide for site-specific delivery of medicinal agents within the GI tract. Moreover, the polymers provide for site-specific imaging of the GI tract.

In accordance with the present invention, there is provided an orally/rectally administrable GI formulation containing an effective amount of a water-insoluble or poorly water-soluble therapeutic agent. There is further provided a method for affecting diseased conditions in the GI tract comprising oral or rectal administration to a patient, an effective amount of the above-identified formulation to prevent or cure such diseased conditions. There is further provided a method and formulation for X-ray diagnostic imaging of the GI tract which includes orally or rectally administering to the patient an effective amount of X-ray contrast compositions.

SUMMARY OF THE INVENTION

In accordance with the present invention, there is provided an orally/rectally administrable therapeutic composition or diagnostic composition comprising:

of from about 0.1% to about 45% w/v of an essentially water-insoluble particulate drug or diagnostic agent having an effective average particle size of less than about 2000 nm, more preferably an effective average particle size of less than about 1000 nm, and most preferably an effective average particle size of less than about 400nm;

of from about 0.1 to about 10.0% w/v, and preferably of from about 1 to about 6% w/v of a bioadhesive stabilizer;

of from about 0.1% to about 5.0% w/v of a long chain linear poly (ethylene oxide) polymer having a molecular weight of from about 100,000 to about 2,000,000 daltons;

water to make 100% w/v.

Secondary stabilizers may also be used in the formulations up to about 1% w/v, preferably up to about 0.2% w/v, and most preferably up to about 0.1% w/v. Secondary stabilizers include dioctylsulfosuccinate (DOSS) and sodium laury sulfate (SLS).

Other ingredients customarily used in oral pharmaceutical or diagnostic formulations may also be included, such as flavorants, colorants and preservatives to provide pharmaceutically acceptable and palatable formulations.

DESCRIPTION OF THE PREFERRED EMBODIMENT

The present invention is the employment of nanoparticles of drug substance stabilized by long chain polyethyleneoxides (PEOs), the latter of which may serve as a bioadhesive agent through physical and chemical interaction with the mucus or mucosal surfaces within the GI tract. It has been shown that incorporation of linear PEOs having a molecular weight of approximately 100,000–2,000,000 into a formulation of nanoparticulate barium sulfate resulted in prolonged retention of the radiopaque in the stomach and duodenum and/or superior coating in the ascending, transverse and descending colon of beagle dogs.

Nanoparticles, described in U.S. Pat. No. 5,145,684, are particles consisting of a poorly soluble therapeutic or diagnostic agent onto which are adsorbed a non-cross linked surface modifier, and which have an average particle size of less than about 400 nanometers (nm). As used herein poorly soluble means that the material has a solubility in aqueous medium of less than about 10 mg/ml, and preferably of less than about 1 mg/ml. Suitable drug substances for use in the present invention are detailed below.

Suitable drug substance can be selected from a variety of known classes of drugs, for example, antacids, anti-inflammatory agents, antibiotics (including penicillins), antimycobacterial agents, antiviral agents, corticosteriods, parasympathomimetics, demulcents, emollients, gastrointestinal protectives and adsorbents, antifungals, H2-blocking agents, proton pump inhibitors, muscarinic antagonists, bismuth compounds, sucralfate, carbenoxolone, prostaglandins, digestants, bile acids, laxatives, antiparasitic agents, anthelmintics, antiprotozoal agents, antimicrobial agents, vitamins, immunologic agents, vaccines, anesthetics, lipid-regulating agents and bile acid sequestrants. Preferred drug substances include those intended for oral administration or rectal administration. A description of these classes of drugs and a listing of species within each class can be found in Martindale, The Extra Pharmacopoeia, Twenty-Ninth Edition, The Pharmaceutical Press, London, 1989. The drug substances are commercially available and/or can be prepared by techniques known in the prior art.

Surfactants found to have bioadhesive or mucoadhesive properties include:
1) Poloxamers which are polyethylene-polypropylene oxide tri-block co-polymers of the formula (polyethylene oxide)$_a$-(polypropylene oxide)$_b$-(polyethylene oxide )$_c$ wherein
   a is 46, 52, 62, 75, 97, 98, 122, and 128;
   b is 16, 30, 35, 39, 47, 54, and 67; and
   c is 46, 52, 62, 75, 97, 98, 122, and 128;
2) polyvinyl alcohol,
3) polyvinyl pyrrolidone,
4) hydroxypropyl methylcellulose, and 5) polyoxyethylene sorbitan mono-oleate (Tween 80).

The particles can be prepared in a method comprising the steps of dispersing a therapeutic or diagnostic agent in a liquid dispersion medium and applying mechanical means in the presence of grinding media to reduce the particle size of the therapeutic or diagnostic agent to an effective average particle size of less than about 400 nm. The particles can be reduced in size in the presence of a surface modifier. Alternatively, the particles can be contacted with a surface modifier after attrition.

As used herein, particle size refers to a number average particle size as measured by conventional particle size measuring techniques well known to those skilled in the art, such as sedimentation field flow fractionation, photon correlation spectroscopy, or disk centrifugation. When photon correlation spectroscopy (PCS) is used as the method of particle sizing the average particle diameter is the Z-average particle diameter known to those skilled in the art. By "an effective average particle size of less than about 400 nm" it is meant that at least 90% of the particles have a weight average particle size of less than about 400 nm when measured by the above-noted techniques. In preferred embodiments, the effective average particle size is less than about 300 nm and more preferably less than about 250 nm. In some embodiments, an effective average particle size of less than about 100 nm has been achieved. With reference to the effective average particle size, it is preferred that at least 95% and, more preferably, at least 99% of the particles have a particle size less than the effective average, 400 nm. In particularly preferred embodiments, essentially all of the particles have a size less than 400 nm. In some embodiments, essentially all of the particles have a size less than 250 nm.

The therapeutic or diagnostic agent selected is obtained commercially and/or prepared by techniques known in the art in a conventional coarse form. It is preferred, but not essential, that the particle size of the coarse therapeutic or diagnostic agent selected be less than about 100 μm as determined by sieve analysis. If the coarse particle size of the therapeutic or diagnostic agent is greater than about 100 μm, then it is preferred that the particles of the therapeutic or diagnostic agent be reduced in size to less than 100 μm using a conventional milling method such as airjet or fragmentation milling.

The mechanical means applied to reduce the particle size of the therapeutic or diagnostic agent conveniently can take the form of a dispersion mill. Suitable dispersion mills include a ball mill, an attritor mill, a vibratory mill, and media mills such as a sand mill and a bead mill. A media mill is preferred due to the relatively shorter milling time required to provide the intended result, i.e., the desired reduction in particle size.

The grinding media for the particle size reduction step can be selected from rigid media preferably spherical or particulate in form having an average size less than about 3 mm and, more preferably, less than about 1 mm. Such media desirably can provide the particles with shorter processing times and impart less wear to the milling equipment. The selection of material for the grinding media is not believed to be critical. We have found that zirconium oxide, such as 95% ZrO stabilized with magnesia, zirconium silicate, glass, and polymeric grinding media provide particles having levels of contamination which are believed to be acceptable for the preparation of pharmaceutical compositions. However, other media, such as stainless steel, titania, alumina, and 95% ZrO stabilized with yttrium, are expected to be useful.

The attrition time can vary widely and depends primarily upon the particular mechanical means and processing conditions selected. For ball mills, processing times of up to five days or longer may be required. On the other hand, processing times of less than 1 day (residence times of one minute up to several hours) have provided the desired results using a high shear media mill.

The particles must be reduced in size at a temperature which does not significantly degrade the therapeutic or diagnostic agent. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Control of the temperature, e.g., by jacketing or immersion of the milling chamber in ice water are contemplated. Processing pressures from about 1 psi (0.07 kg/cm$^2$) up to about 50 psi (3.5 kg/cm$^2$) are contemplated. Processing pressures from about 10 psi (0.7 kg/cm$^2$) to about 20 psi (1.4 kg/cm$^2$) are typical.

EXAMPLES

In order to assess the efficiency of mucosal coating throughout the GI tract, nanoparticle formulations of barium sulfate (15% w/v) were prepared in the presence of various polymeric stabilizers and administered (10 ml/kg) to anesthetized beagle dogs via gastric tubation. At 15 minutes post-dose, an equivalent volume of air was administered in order to create a double contrast effect. Animals were then placed in the dorsal recumbent position after which radiographs of the GI tract were generated (15, 30, 45, 60, 120, 240 minutes post-dose) following ventral-dorsal X-ray exposure. Resulting radiographs were developed and evaluated in order to determine the persistence of coating throughout the GI tract.

Resulting radiographs revealed an unexpected synergy between polymeric stabilizers (linear, high molecular weight, polyethylene oxide polymers [PEO's] and ethylene oxide-propylene oxide tri-block co-polymers [poloxamers]) as indicated by the retention of nanoparticulate material in the extreme upper GI tract (i.e., stomach and descending duodenum) and/or the colon for prolonged periods. Such efforts were not realized; however, in the case of poloxamers alone, which provided for excellent overall coating of the GI tract throughout much of the small intestine, while demonstrating limited ability to coat the regions specified above. Moreover, employment of PEO's alone did not result in suitable particle size reduction, a factor which had previously been shown to be of paramount importance in promoting adhesion of particulate material to the mucosal surfaces of the GI tract.

The poly(ethylene oxide) polymers are non-ionic water soluble resins. They are available from Union-Carbide in a wide variety of molecular weights. In the present invention molecular weights over 2,000,000 for PEO's are not effective as the resulting composition is too viscous to administer. The poloxamers are available as Pluronics from BASF Corporation and have moecular weight less than 20,000. The poloaxmers are shown by the manufacturer-designated number.

Tables I and II illustrate the persistence of mucosal coating in the vicinity of the stomach and descending duodenum in the presence and absence of PEO's. Resulting radiographs were evaluated in accordance with the following grading scheme:

Stomach and Duodenum

+++ indicates extensive coating of the stomach and/or descending duodenum

++ indicates moderate coating of the stomach and/or descending duodenum

+ indicates minor coating of the stomach and/or descending duodenum

− indicates absence of coating of the stomach and/or descending duodenum

Colon

+++ Indicates coating of the ascending, transverse and descending colon

++ Indicates coating of ⅔ of the colon

+ Indicates coating of ⅓ of the colon

− Indicates absence of coating of the colon.

TABLE I

Coating Efficiency of a 15% w/v Nanoparticulate Barium Sulfate Formulation Stabilized by 4% w/v Pluronic F108

| | Coating Efficiency | | | | | |
|---|---|---|---|---|---|---|
| | Stomach | | Duodenum | | Colon | |
| Time (min) | Subject A | Subject B | Subject A | Subject B | Subject A | Subject B |
| 15 | +++ | +++ | ++ | +++ | − | − |
| 30 | +++ | +++ | + | ++ | − | − |
| 45 | +++ | +++ | + | ++ | − | − |
| 60 | ++ | +++ | + | + | − | − |
| 120 | + | ++ | − | + | − | + |
| 240 | − | − | − | − | ++ | ++ |

TABLE II

Coating Efficiency of a 15% w/v Nanoparticulate Barium Sulfate Formulation Stabilized by 3% w/v Pluronic F108 and 1% w/v POLYOX WSRN-750

| | Coating Efficiency | | | | | |
|---|---|---|---|---|---|---|
| | Stomach | | Duodenum | | Colon | |
| Time (min) | Subject A | Subject B | Subject A | Subject B | Subject A | Subject B |
| 15 | +++ | n/a | +++ | n/a | − | n/a |
| 30 | +++ | n/a | +++ | n/a | − | n/a |
| 45 | +++ | n/a | +++ | n/a | − | n/a |
| 60 | +++ | n/a | +++ | n/a | − | n/a |
| 120 | ++ | n/a | − | n/a | − | n/a |
| 240 | + | n/a | − | n/a | − | n/a |

*n/a indicates that data is not available

These examples demonstrate clearly that persistence of mucosal coating is prolonged in the upper regions of the small intestine when barium sulfate nanoparticles are stabilized by both Pluronic F108 and POLOX WSNR-750, particularly at time points in excess of 45 minutes. Such effects are further evidenced by the delayed appearance of nanoparticulate material in the colon, consistent with a longer residence time in the small bowel. Similar results were obtained when a blend of Pluronic F127 and POLOX WSNR-750 was utilized to promote site-specific adhesion of barium sulfate nanoparticles to the stomach and duodenum (see Tables III and IV).

TABLE III

Coating Efficiency of a 15% w/v Nanoparticulate Barium Sulfate Formulation Stabilized by 4% w/v Pluronic F127

| | Coating Efficiency | | | | | |
|---|---|---|---|---|---|---|
| | Stomach | | Duodenum | | Colon | |
| Time (min) | Subject A | Subject B | Subject A | Subject B | Subject A | Subject B |
| 15 | +++ | +++ | ++ | + | – | – |
| 30 | +++ | +++ | + | + | – | – |
| 45 | +++ | +++ | – | + | – | – |
| 60 | ++ | ++ | – | – | – | – |
| 120 | + | ++ | – | – | ++ | ++ |
| 240 | – | – | – | – | ++ | + |

TABLE IV

Coating Efficiency of a 15% w/v Nanoparticulate Barium Sulfate Formulation Stabilized by 3% w/v Pluronic F127 and 1% w/v POLYOX WSRN-750

| | Coating Efficiency | | | | | |
|---|---|---|---|---|---|---|
| | Stomach | | Duodenum | | Colon | |
| Time (min) | Subject A | Subject B | Subject A | Subject B | Subject A | Subject B |
| 15 | +++ | +++ | +++ | +++ | – | – |
| 30 | +++ | +++ | ++ | ++ | – | – |
| 45 | +++ | + | ++ | ++ | – | – |
| 60 | +++ | + | ++ | ++ | – | – |
| 120 | ++ | + | ++ | ++ | – | – |
| 240 | – | – | – | – | ++ | + |

In the case of Pluronic F98 and POLOX WSNR-750; however, a slightly different effect was realized. While combination of polymers resulted in prolonged retention of barium sulfate nanoparticles in the stomach, a comparatively weak effect was observed in the descending duodenum, where only a moderate improvement in mucoadhesion was achieved. However, the combination later provided for improved mucoadhesion in the colonic region of the same animals as evidenced by extensive coating of the ascending, transverse and descending colonic loops of both animals at 4 hours post administration.

TABLE V

Coating Efficiency of a 15% w/v Nanoparticulate Barium Sulfate Formulation Stabilized by 4% w/v Pluronic F98

| | Coating Efficiency | | | | | |
|---|---|---|---|---|---|---|
| | Stomach | | Duodenum | | Colon | |
| Time (min) | Subject A | Subject B | Subject A | Subject B | Subject A | Subject B |
| 15 | +++ | +++ | – | + | – | – |
| 30 | n/a | ++ | n/a | + | n/a | – |
| 45 | + | ++ | – | – | – | – |
| 60 | + | + | – | – | – | – |
| 120 | + | – | – | – | ++ | + |
| 240 | – | – | – | – | + | ++ |

*n/a indicates that data is not available

TABLE VI

Coating Efficiency of a 15% w/v Nanoparticulate Barium Sulfate Formulation Stabilized by 3% w/v Pluronic F98 and 1% w/v POLYOX WSRN-750

| | Coating Efficiency | | | | | |
|---|---|---|---|---|---|---|
| | Stomach | | Duodenum | | Colon | |
| Time (min) | Subject A | Subject B | Subject A | Subject B | Subject A | Subject B |
| 15 | +++ | +++ | – | ++ | – | – |
| 30 | +++ | +++ | – | ++ | – | – |
| 45 | +++ | +++ | – | + | – | – |
| 60 | ++ | +++ | – | + | – | – |
| 120 | ++ | +++ | – | – | +++ | ++ |
| 240 | – | + | – | – | +++ | +++ |

In the examples described above it is apparent that site-specificity can be altered by adjusting the type and amount of PEO and poloxamer. Thus, a therapeutic formulation can be delivered in a site specific manner to the stomach, duodenum or colon.

While there has been shown and described what are at present considered to be the preferred embodiments of the present invention, various alterations and modifications may be made herein. All such modifications are intended to be included within the scope of the appended claims.

What is claimed is:

1. An orally/rectally administerable therapeutic or diagnostic X-ray formulation comprising:
   (A) of from about 0.1% to about 45% of an essentially water insoluble particulate radiopaque crystalline material or drug having an effective average particle size of less than about 2000 nm;
   (B) of from about 0.1 to about 10.0% w/v of a bioadhesive polymeric stabilizer selected from the group consisting of:
      (i) polyethylene-polypropylene oxide tri-block co-polymers of the formula;
         (polyethylene oxide)$_a$-(polypropylene oxide)$_b$-(polyethylene oxide)$_c$ wherein
         a is 46, 52, 62, 75, 97, 98, 122, or 128;
         b is 16, 30, 35, 39, 47, 54, or 67; and
         c is 46, 52, 62, 75, 97, 98, 122, or 128;
      (ii) polyvinyl alcohol, (iii) polyvinyl pyrrolidone,
(iv) hydroxypropyl methylcellulose, and
(v) polyoxyethylene sorbitan mono-oleate;

(C) of from about 0.1 to about 5.0 w/v of a long chain linear poly (ethylene oxide) polymer having a molecular weight of from about 100,000 to about 2,000,000 daltons; and (D) water to make 100% w/v.

2. The therapeutic formulation of claim 1 wherein said drug is selected from the group consisting of: antacids, anti-inflammatory agents, antibiotics, antimycobacterial agents, antiviral agents, corticosteriods, parasympathomimetics, demulcents, emollients, gastrointestinal protectives and adsorbents, antifungals, H2-blocking agents, proton pump inhibitors, muscarinic antagonists, bismuth compounds, sucralfate, carbenoxolone, prostaglandins, digestants, bile acids, laxatives, antiparasitic agents, anthelmintics, antiprotozoal agents, antimicrobial agents, vitamins, immunologic agents, vaccines, anesthetics, lipid-regulating agents and bile acid sequestrants.

3. The therapeutic formulation of claim 1 wherein the effective average particle size is less than about 1000 mn.

4. The therapeutic formulation of claim 1 wherein the effective average particle size is less than about 400 nm.

5. An orally/rectally administerable gastrointestinal diagnostic X-ray formulation comprising:

(A) of from about 0.1% to about 45% of an essentially water insoluble particulate radiopaque crystalline material having an effective average particle size of less than about 2000 nm;

(B) of from about 0.1 to about 10.0% w/v of a bioadhesive polymeric stabilizer selected from the group consisting of:
(i) polyethylene-polypropylene oxide tri-block co-polymers of the formula;
(polyethylene oxide)$_a$-(polypropylene oxide)$_b$-(polyethylene oxide)$_c$ wherein
a is 46, 52, 62, 75, 97, 98, 122, or 128;
b is 16, 30, 35, 39, 47, 54, or 67; and
c is 46, 52, 62, 75, 97, 98, 122, or 128;
(ii) polyvinyl alcohol,
(iii) polyvinyl pyrrolidone,
(iv) hydroxypropyl methylcellulose, and
(v) polyoxyethylene sorbitan mono-oleate;

(C) of from about 0.1 to about 5.0 w/v of a long chain linear poly (ethylene oxide) polymer having a molecular weight of from about 100,000 to about 2,000,000 daltons; and (D) water to make 100% w/v.

6. The orally/rectally administrable gastrointestinal diagnostic X-ray contrast formulation of claim 5 wherein said radiopaque crystalline material is selected from the group consisting of: 3,5-Bis-acetylamino-2,4,6-triiodo-benzoic acid ethyl ester (WIN 05316), 2-(3,5-Bis-acetylamino-2,4,6-triiodobenzyloxy)-2-methyl malonic acid (WIN 67975), propanedioic acid, [[3,5-Bis-(acetylamino)-2,4,6-triiodo-benzyl]oxy]-bis(1-methylethyl) ester acid ethyl ester (WIN 68165], Diethyl 5-acetylamino-2,4,6-triiodoisophthalate (WIN 59316), ethyl 3,5-bis(acetylamino)-2,4,6-triiodobenzoate (WIN 8883), bis-[1-(ethoxycarbonyl)propyl]-2,4,6-triiodo-5-acetylamino-isophthalate (WIN 68183), 1,3,5-triethyl-2,4,6-triiodobenzene (WIN 68756), 3,5-Bis-acetylamino-2,4,6-triiodo-benzoic acid 4-methoxy-benzyl ester (WIN 67754), 3,5-Bis-acetylamino-2,4,6-triiodo-benzoic acid 4-isopropyl benzoate ester (WIN 67956), (6-ethoxy-6-oxohexyl 3,5-bis(acetylamino)2,4,6-triiodo-benzoate (WIN 67722), and 3,5-Bis-acetylamino-2,4,6-triiodo-benzoic acid 5-isopropoxycarbonyl-pentylester (WIN 67995).

7. The orally/rectally administrable gastrointestinal diagnostic X-ray contrast formulation of claim 5 wherein said particulate radiopaque crystalline material is selected from the group consisting of:
barium sulfate, barium hexaborite, barium chromite, barium fluogallate, barium tri-ortho phosphate, barium metasilicate, barium titanate and barium zirconate.

8. The formulation of claim 5 wherein the effective average particle size is less than about 1000 nm.

9. The formulation of claim 5 wherein the effective average particle size is less than about 400 nm.

10. A method of carrying out X-ray examination of the gastrointestinal tract of a patient, the method comprising orally/rectally administering to the patient an X-ray contrast composition comprising:

(A) of from about 0.1% to about 45% of an essentially water insoluble particulate radiopaque crystalline material having an effective average particle size of less than about 2000 nm;

(B) of from about 0.1 to about 10.0% w/v of a bioadhesive polymeric stabilizer selected from the group consisting of:
(i) polyethylene-polypropylene oxide tri-block co-polymers of the formula;
(polyethylene oxide)$_a$-(polypropylene oxide)$_b$-(polyethylene oxide)$_c$ wherein
a is 46, 52, 62, 75, 97, 98, 122, or 128;
b is 16, 30, 35, 39, 47, 54, or 67; and
c is 46, 52, 62, 75, 97, 98, 122, or 128;
(ii) polyvinyl alcohol,
(iii) polyvinyl pyrrolidone,
(iv) hydroxypropyl methylcellulose, and
(v) polyoxyethylene sorbitan mono-oleate;

(C) of from about 0.1 to about 5.0 w/v of a long chain linear poly (ethylene oxide) polymer having a molecular weight of from about 100,000 to about 2,000,000 daltons; and (D) water to make 100% w/v.

11. The method of carrying out X-ray examination of the gastrointestinal tract of a patient according to claim 10 wherein said X-ray contrast composition is selected from the group consisting of: 3,5-Bis-acetylamino-2,4,6-triiodo-benzoic acid ethyl ester (WIN 05316), 2-(3,5-Bis-acetylamino-2,4,6-triiodo-benzyloxy)- 2-methyl malonic acid (WIN 67975), propanedioic acid, [[3,5-Bis-(acetylamino)-2,4,6-triiodo-benzyl]oxy]-bis(1-methylethyl) ester acid ethyl ester (WIN 68165), Diethyl 5-acetylamino-2,4,6-triiodo-isophthalate (WIN 59316), ethyl 3,5-bis(acetylamino)-2,4,6-triiodobenzoate (WIN 8883), bis-[1-(ethoxycarbonyl)propyl]-2,4,6-triiodo-5-acetylamino-isophthalate (WIN 68183), 1,3,5-triethyl-2,4,6-triiodobenzene (WIN 68756), 3,5-Bis-acetylamino-2,4,6-triiodo-benzoic acid 4-methoxy-benzyl ester (WIN 67754), 3,5-Bis-acetylamino-2,4,6-triiodo-benzoic acid 4-isopropyl benzoate ester (WIN 67956), (6-ethoxy-6-oxohexyl 3,5-bis(acetylamino)2,4,6-triiodo-benzoate (WIN 67722), and 3,5-Bis-acetylamino-2,4,6-triiodo-benzoic acid 5-isopropoxycarbonyl-pentylester (WIN 67995).

12. The method of carrying out X-ray examination of the gastrointestinal tract of a patient according to claim 10 wherein said particulate radiopaque crystalline material is selected from the group consisting of barium sulfate, barium hexaborite, barium chromite, barium fluogallate, barium tri-ortho phosphate, barium metasilicate, barium titanate and barium zirconate.

13. The method of claim 10 wherein the effective average particle size of the radiopaque crystalline material is less than about 1000 nm.

14. The method of claim 10 wherein the effective average particle size of the radiopaque crystalline material is less than about 400 nm.

15. The orally/rectally administerable gastrointestinal diagnostic X-ray formulation of claim 5, wherein:

the essentially water insoluble particulate radiopaque crystalline material is barium sulfate and the bioadhesive polymeric stabilizer is Pluronic F108 which is a polyethylene-polypropylene oxide tri-block co-polymer.

\* \* \* \* \*